(12) United States Patent
Trotter et al.

(10) Patent No.: US 6,633,626 B2
(45) Date of Patent: Oct. 14, 2003

(54) METHODS AND APPARATUS FOR CORRECTING SCATTER

(75) Inventors: Dinko E. Gonzalez Trotter, Clifton Park, NY (US); Bernhard Erich Hermann Claus, Niskayuna, NY (US); Serge Louis Wilfrid Muller, Guyancourt (FR)

(73) Assignee: General Electric Company, Schenectady, NY (US)

( * ) Notice: Subject to any disclaimer, the term of this patent is extended or adjusted under 35 U.S.C. 154(b) by 8 days.

(21) Appl. No.: 10/062,338

(22) Filed: Feb. 1, 2002

(65) Prior Publication Data

US 2003/0147491 A1 Aug. 7, 2003

(51) Int. Cl.$^7$ ................................................ A61B 6/00
(52) U.S. Cl. .......................................... 378/62; 378/37

(58) Field of Search ............................. 378/37, 62, 98, 378/98.2, 901

(56) References Cited

U.S. PATENT DOCUMENTS

| | | | |
|---|---|---|---|
| 4,918,713 A | | 4/1990 | Honda |
| 5,293,195 A | * | 3/1994 | Berlad et al. ................. 378/87 |
| 5,440,647 A | | 8/1995 | Floyd, Jr. et al. |
| 6,104,777 A | | 8/2000 | Darboux et al. |
| 6,256,370 B1 | | 7/2001 | Yavuz |
| 6,269,176 B1 | * | 7/2001 | Barski et al. ................ 382/128 |
| 6,353,674 B1 | * | 3/2002 | Dewaele ..................... 382/132 |

* cited by examiner

*Primary Examiner*—David V. Bruce
(74) *Attorney, Agent, or Firm*—Armstrong Teasdale LLP

(57) ABSTRACT

A method for removing scatter in an image includes acquiring data of an object of interest, and using an iterative equation including a thickness-dependent kernel modulation factor to reconstruct an image of the object.

35 Claims, 6 Drawing Sheets

Scatter away from the boundary of the breast (top diagram) and scatter near the edge of the breast (bottom diagram)

Slit collimator geometry used to obtain scatter-free profiles.

Profiles for detector pixels directly underneath the slit collimator. The scatter-corrected profile was not corrected for kernel asymmetry.

Profiles for detector pixels directly underneath the slit collimator. The scatter-corrected profile includes kernel asymmetry correction.

Comparison of profiles across the raw image, the direct events image and the scatter-corrected image after eight iterations.

Comparison of image profiles of measured scatter signal and calculated scatter signal.

Comparison of profiles for a raw and scatter-corrected images. The scatter fraction near the lead beamstop was ~0.62.

METHODS AND APPARATUS FOR CORRECTING SCATTER

STATEMENT REGARDING FEDERALLY SPONSORED RESEARCH & DEVELOPMENT

The government may have rights in this invention pursuant to Subcontract 22287 issued from the Office of Naval Research/Henry M. Jackson Foundation.

BACKGROUND OF THE INVENTION

This invention relates generally to X-ray image processing and more particularly to methods and apparatus for performing a scatter correction algorithm.

At least some known imaging systems use a moving grid of parallel metal plates to facilitate a scatter-signal suppression. The grid rejects a majority of photons that are not essentially parallel to a beam emanating from an X-ray source in a direction of a detector, based on the scatter grid geometry. Since many scattered photons are not parallel to the X-ray beam, a significant proportion of scatter events are absorbed by the grid. In addition to absorbing scatter events, the grid also absorbs a significant portion of the non-scattered, or primary photons. When a scatter grid is used, approximately 20% of the remaining signal is scatter, and approximately 30% of the primary events are rejected. Scatter grid assemblies are also expensive and mechanically complex.

BRIEF DESCRIPTION OF THE INVENTION

In one aspect, a method for removing scatter in an image is provided. The method includes acquiring data of an object of interest, and using an iterative equation including a thickness-dependent kernel modulation factor to reconstruct an image of the object.

In another aspect, a method for removing scatter in an image is provided. The method includes acquiring data of an object of interest, and using an iterative equation to reconstruct an image of the object when a scatter fraction greater than approximately 0.5.

In a further aspect, a computer readable medium encoded with a program executable by a computer for removing scatter in an image is provided. The program is configured to instruct the computer to acquire data of an object of interest, and use an iterative equation including a thickness-dependent kernel modulation factor to reconstruct an image of the object.

In a still another aspect, a medical imaging system for removing scatter in an image is provided. The medical imaging system includes a detector array, at least one radiation source, and a computer coupled to said detector array and radiation source and configured to acquire data of an object of interest, and use an iterative equation to reconstruct an image of the object when a scatter fraction is greater than approximately 0.5.

DETAILED DESCRIPTION OF THE INVENTION

Figure 1:
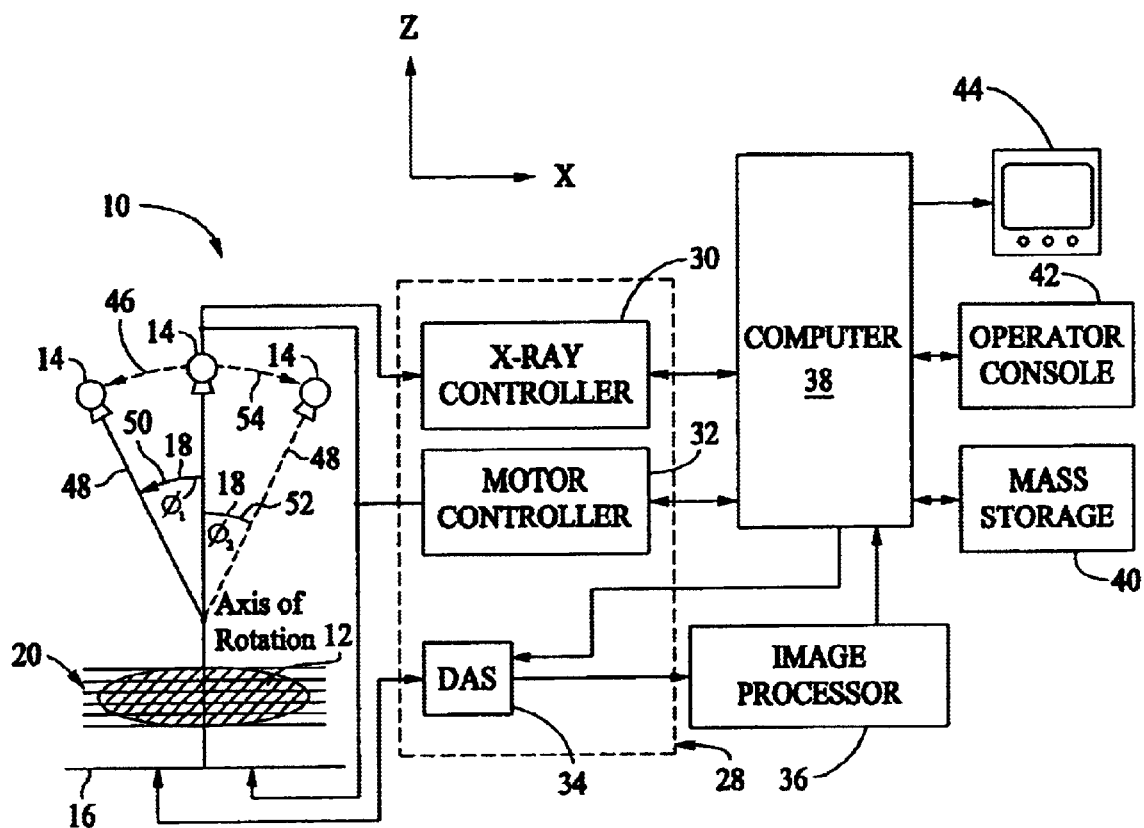
FIG. 1 is a pictorial view of an imaging system.

FIG. 1 is a pictorial view of an imaging system 10, such as a X-ray mammography imaging system and a tomosynthesis imaging system. System 10 includes at least one radiation source 14, such as an X-ray source, and at least one detector array 16 for collecting views from a single or a plurality of projection angles 18. Specifically, system 10 includes a radiation source 14 which projects a cone-shaped beam of X-rays which pass through object 12 and impinge on detector array 16. Detector array 16 is fabricated in a panel configuration having a plurality of pixels (not shown) arranged in rows and columns such that an image is generated for an entire object 12 of interest. In one embodiment, for example for imaging of the lung, detector array 16 is a chest detector array 16 and object 12 is a patient's chest 12. In an exemplary embodiment, imaging system 10 is used to generate a three-dimensional dataset representative of an imaged object 12. The views obtained at each angle 18 may be used to reconstruct a plurality of slices, i.e., images representative of structures located in planes 20 which are parallel to detector 16. In another embodiment, only a single projection radiograph of the object of interest is acquired.

Each pixel includes a photosensor, such as a photodiode (not shown), that is coupled via a switching transistor (not shown) to two separate address lines (not shown). In one embodiment the two lines are a scan line and a data line. The radiation incident on a scintillator material and the pixel photosensors measure, by way of change in the charge across the diode, an amount of light generated by X-ray interaction with the scintillator. More specifically, each pixel produces an electronic signal that represents an intensity and/or scatter, after attenuation by object 12, of an X-ray beam impinging on detector array 16. In one embodiment, detector array 16 is approximately 20 centimeters (cm) by 20 cm and is configured to produce views for an entire object 12 of interest. Alternatively, detector array 16 is variably sized depending on the intended use. Additionally, a size of the individual pixels on detector array 16 is selected based on the intended use of detector array 16.

In the exemplary embodiment, alternative detector technology is used, such that views in digital form are generated by detector 16. In another embodiment, the reconstructed three-dimensional dataset is not arranged in slices corresponding to planes that are parallel to detector 16, but in a more general fashion. In yet another embodiment, detector 16 is a shape other than planar.

In the exemplary embodiment, radiation source 14 and detector array 16 are moveable relative to the object 12 and each other. More specifically, radiation source 14 and detector array 16 are movable such that the projection angle 18 of the imaged volume is altered. Radiation source 14 and detector array 16 are movable such that projection angle 18 may be any acute or oblique projection angle.

The operation of radiation source 14 is governed by a control mechanism 28 of imaging system 10. Control mechanism 28 includes a radiation controller 30 that provides power and timing signals to radiation source 14 and a motor controller 32 that controls a respective movement speed and position of radiation source 14 and detector array 16. A data acquisition system (DAS) 34 in control mechanism 28 samples digital data from detector 16 for subsequent processing. A portion of the data acquired includes a compressed breast thickness, which is included along with a detector cover thickness and a compression paddle thickness, which are then used as parameters in the scatter correction process. The measured image and breast thickness information are processed to form a "breast thickness map" which is included in the scatter correction process. An image processor 36 receives a sampled and digitized projection dataset from DAS 34 and performs image processing and scatter correction, as described herein. In one embodiment, image processor 36 also performs 3D reconstruction of imaged object 12 using scatter-corrected projection images. The scatter-corrected images, and/or the reconstructed three-dimensional dataset, representative of imaged object 12, is applied as an input to a computer 38 which stores the datasets in a mass storage device 40. Image processor 36 is programmed to perform functions described herein, and, as used herein, the term image processor refers to computers, processors, microcontrollers, microcomputers, programmable logic controllers, application specific integrated circuits, and other programmable circuits.

Computer 38 also receives commands and scanning parameters from an operator via console 42 that has an input device. A display 44, such as a cathode ray tube, and a liquid crystal display (LCD), allows the operator to observe the reconstructed three-dimensional dataset and other data from computer 38. The operator supplied commands and parameters are used by computer 38 to provide control signals and information to DAS 34, motor controller 32, and radiation controller 30. In one embodiment, the compressed breast thickness is not acquired by system 10, but entered by an operator via console 42.

In one embodiment, a patient is positioned such that the object of interest is within the field of view of system 10, i.e., object 12 is positioned within the imaged volume extending between radiation source 14 and detector array 16. Views of object 12, are then acquired from at least two projection angles 18 to generate a projection dataset of the volume of interest. The plurality-of-views represent the tomosynthesis projection dataset. The collected projection dataset is then utilized to generate a three-dimensional dataset, i.e., a plurality of slices for scanned object 12, such as a breast 12, wherein the three-dimensional dataset is representative of the three-dimensional radiographic representation of imaged breast 12. After enabling radiation source 14 so that the radiation beam is emitted at first projection angle 50, a view is collected using detector array 16. Projection angle 18 of system 10 is then altered by translating the position of source 14 so that central axis 48 of the radiation beam is altered to a second projection angle 52 and position of detector array 16 is altered such that breast 12 remains within the field of view of system 10. Radiation source 14 is again enabled and a view is collected for second projection angle 52. The same procedure is then repeated for any number of subsequent projection angles 18.

Some known imaging systems 10 rely on a differential absorption of X-rays by a plurality of tissue types. For example, X-ray mammography relies on differential absorption of tissue types found in a human breast 12. X-ray photons that are directly transmitted (i.e. primary photons) through object 12 are detected by a film, or by digital detector 16.

In addition to interacting with matter through absorption, X-rays also undergo scattering with the electronic constituents of object 12 being imaged and other components of X-ray imaging system 10. For example, in X-ray mammography, a majority of photon scatter occurs in breast 12, a compression paddle (not shown) and a plurality of detector materials (not shown). Scattered photons produce a low-frequency "haze" superimposed on the image produced by primary X-ray photons due partially to their nearly isotropic scattering cross section. A signal from scattered photons contributes to the overall noise of the image and contributes to a decrease in an image contrast. In some known imaging systems 10, approximately 40% of the signal in a typical mammogram, i.e. using a breast 12 approximately 4 centimeters (cm) in compressed breast thickness, is composed of scattered events, if a scatter grid (not shown) is not used. For breasts 12 thicker than approximately 6 cm, the scatter fraction (scatter/total signal) may be over 0.5.

In one embodiment, an acquired x-ray image is processed such that the contribution to the image due to scattered x-ray photons is essentially removed. In yet another embodiment, the scatter-corrected images may be used to quantitatively link the image signal to radiographic characteristics of the constituent tissue components of the imaged object.

The scatter-correction algorithm described herein facilitates eliminating the need for using the scatter grid in X-ray mammographic imaging. Further, scatter-corrected images according to the present invention show a mean absolute deviation of approximately 3% with respect to scatter-free images, even in the boundary region of breast 12. Therefore, resulting in superior contrast with respect to a Smit-Roentgen scatter grid mammography result, wherein approximately 20% of the remaining signal is due to scatter. In one embodiment, the algorithm described herein may be applied to scatter correction of tomosynthesis projection datasets where a standard scatter grid cannot be used. Further, the scatter correction algorithm facilitates scatter-correction in other X-ray applications, such as, but not limited to, a tissue density decomposition for a plurality of two-dimensional (2D) and three-dimensional (3D) applications.

In one embodiment, an image y is formed by combining primary events and scatter events. Primary events are photons which travel directly from source 14 to detector 16, and scatter events are photons that scatter from object 12 being imaged or any other object in the path of the X-ray beam into detector 16. An image y may be defined according to:

$$y = b + s, \qquad \text{Equation 1}$$

where b is an image formed by unattenuated photons, i.e. primary events, and s is an image formed by photons scattered into detector 16, i.e. scatter events.

To recover a direct image b, term s may be modeled as a convolution between a scatter kernel p and the direct image b, according to:

$$s = p*b, \qquad \text{Equation 2}$$

where * is a convolution operator.

Using Equations 1 and 2, image y may be defined according to:

$$y = b + p*b \qquad \text{Equation 3}$$

For any given pixel j in image y, Equation 3 may be expressed as:

$$y_j = b_j + \sum_{k=1}^{n} p_{jk} b_k \qquad \text{Equation 4}$$

where an index k spans all pixels of detector 16, i.e. pixel 1 through pixel n, and a factor, or kernel, $p_{j,k}$ relates the number of direct events detected in pixel j to a contribution of photons originally going to pixel k.

In one embodiment, the factor, or kernel $p_{j,k}$ is spatially invariant such that $p_{j,k}=p_{j-k}$, where j–k includes distance and directional information. For a spatially invariant kernel, a convolution translates into a simple product in Fourier space, which may be numerically calculated through Fourier Transforms, such as, but not limited to, a Fast Fourier Transforms (FFT). For example, the second term in Equation 4 may be calculated through a FFT, if the kernel $p_{j,k}$ is spatially invariant. In another embodiment, $p_{j,k}$ is not spatially invariant, and the second term in Equation 4 is not calculated using a FFT. The assumption of a spatially-invariant scatter kernel is a good approximation in the case of scatter within a single slab or a plurality of slabs, wherein the slabs include a homogeneous material and a constant thickness, and extend approximately horizontally beyond the X-ray beam emanating from radiation source 14 and impinging on detector array 16, and wherein the slabs are resting on detector 16 surface with X-ray photons incident approximately perpendicular to the slab's surface. For the slab geometry, the scatter kernel is mainly dependent on the thickness of the material, and only weakly dependent on the material's composition for fatty through glandular-equivalent breast material, and on an X-ray energy spectrum for typical X-ray techniques used in mammography.

The assumption of space invariance in the kernel may introduce inaccuracies in the calculation of the scatter signal when there are large variations of thickness in object 12 being imaged, such as in mammography near the edge of breast 12. Also, there is a significant contribution of scatter events from the detector materials which are irradiated directly by the X-ray beam, i.e. a region outside the edges of breast 12 in a mammography image.

Figure 2:
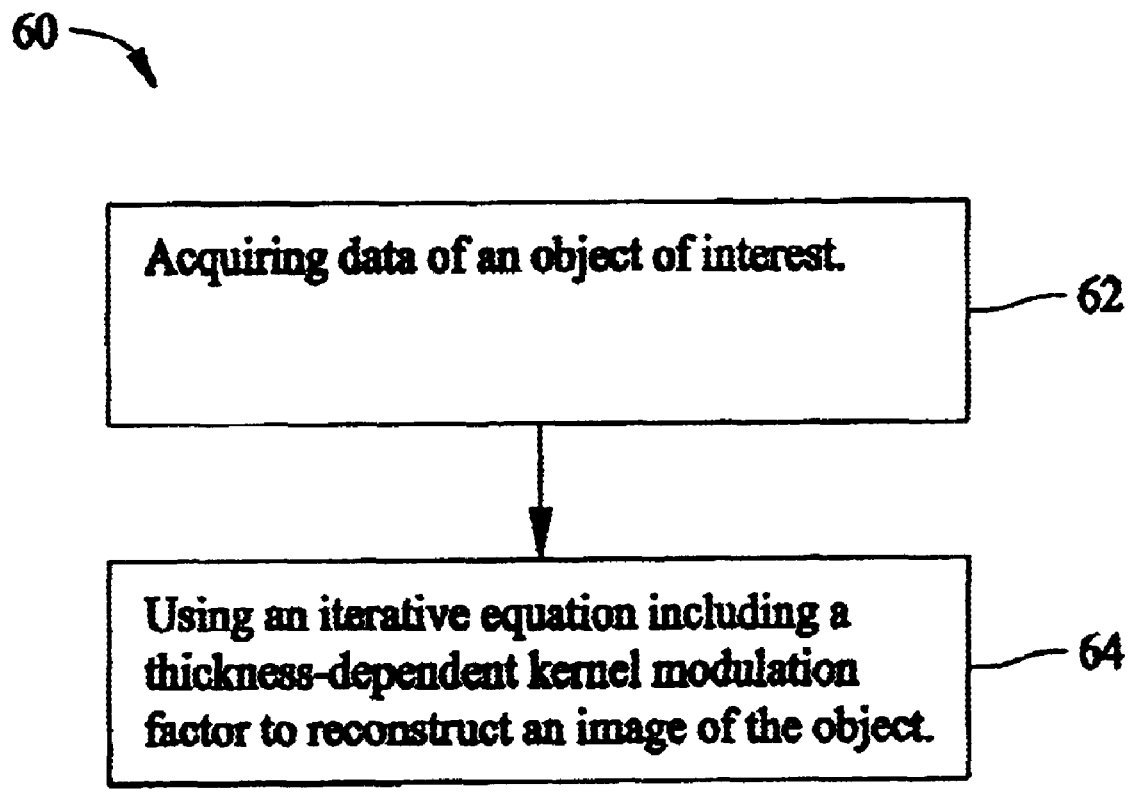
FIG. 2 is a flow diagram of a method for removing scatter.

FIG. 2 is a flow diagram of a method 60 for removing scatter in an image. Method 60 includes acquiring 62 data of object 12 of interest, and using 64 an iterative equation including a thickness-dependent kernel modulation factor to reconstruct an image of the object.

In the exemplary embodiment, a thickness-dependent kernel modulation factor $\alpha_k$, is defined as:

$$a_k = \frac{\bar{p}_k}{\bar{p}_{k_0}}, \qquad \text{Equation 5}$$

where $\bar{p}_k$ is a norm of scatter kernel p, for each pixel k, of detector 16, which is a function of a thickness of material $d_k$, i.e. breast thickness map, traversed by the primary ray incident on the pixel k. Additionally, $\bar{p}_{j_k}$ is the norm of the kernel for the compressed thickness of breast 12, i.e., the distance between a compression paddle and detector 16 surface, and any additional thickness of material due to detector 16 and the compression plate assembly $d_{k_0}$, which can be read out using imaging system 10 or estimated by an alternative means.

The image y, as defined in Equation 3, is re-defined according to:

$$y=b+p*(ab) \qquad \text{Equation 6}$$

where the kernel p is calculated assuming a thickness $d_{k_0}$.
A scatter signal may then be defined according to:

$$s_j = \sum_k p_{jk} a_k b_k, \qquad \text{Equation 7}$$

where each contribution of the scatter events from pixel k to pixel j is re-normalized to account for a change in a detection probability of the scatter event based on a change of thickness of breast 12 material traversed by a ray k. In another embodiment, modulation factor $\alpha_k$ is also dependent on pixel j.

As described previously herein, the norm of the scatter kernel is sensitive to the thickness of material in a slab arrangement, but the shape, as characterized, e.g., by a full-width half-maximum or other parameters, of the scatter kernel is relatively insensitive to the thickness of the uniform slab within a thickness range of approximately 0.3 centimeters (cm) to approximately 10 cm. Therefore, the thickness dependent kernel modulation factor $\alpha_k$ facilitates compensating for a majority of the change in detection probability of a scatter event due to a variable thickness of object 12, and enables the use of space-invariant scatter kernels for accurate scatter correction.

Figure 3:
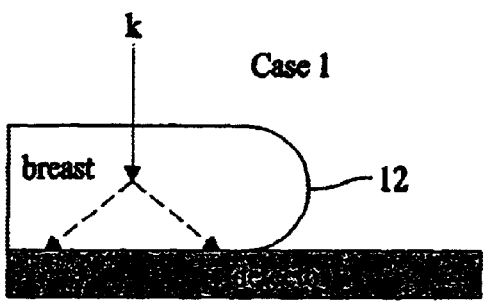
FIG. 3 is an illustration of scatter distribution using a typical imaging system shown.
Figure 3:
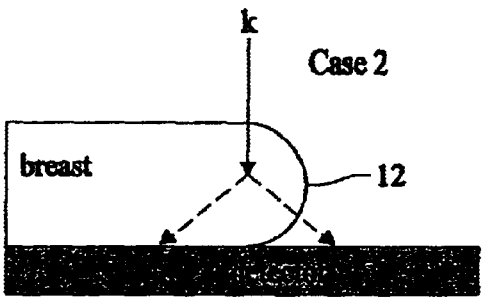

FIG. 3 is an illustration of scatter distribution using a typical imaging system 10. In one embodiment, the scatter kernel $p_{j,k}$, i.e., a space-invariant scatter kernel, is modeled by a radially symmetric function. Approximating scatter using a radially symmetric function is used when the scatter signal is calculated away from the boundaries of breast 12. For example, and referring to FIG. 3, a kernel asymmetry is introduced near breast 12 boundary by photons scattered outside breast 12 that travel through less breast material before being detected. Therefore, in case 1 $p_{j,k}=p_{j'k}$, but in case 2 $p_{j,k}<p_{j'k}$ where in case 1 the distance traversed by a scattered X-ray photon through tissue is the same for pixels j and j', but in case 2 the distance traveled through tissue to pixel j is longer than for pixel j' (pixel j is inside the breast and pixel j' is outside the breast). Therefore in case 2 the X-ray photon scattered into pixel j' is attenuated less than in case 1. Taking this effect into account directly in a kernel calculation facilitates eliminating the spatial invariance of the kernel, but prohibits the use of FFTs in the convolution operation to calculate the scatter signal.

In the exemplary embodiment, a re-nonmalization map is based on the measured image, which is then processed to find the boundary of breast 12. The pixel distance away from the boundary of breast 12 is used to approximate the kernel asymmetry effect without introducing space-variance in the kernel. The re-normalization map N(m) is estimated for every pixel m outside of breast 12 boundary by calculating a distance $d_b(m)$ between pixel m and a closest pixel belonging to breast 12 boundary.

The re-normalization map N(m) may be approximated according to:

$$N(m) \sim e^{\mu d_b(m)}, \qquad \text{Equation 8}$$

where $\mu$ is a mean attenuation coefficient for the X-ray photon spectrum in 50% glandular/50% fat breast equivalent material. In one embodiment, N(mn)=1 for pixels inside breast 12, since most of the X-ray photons scattered within the breast region are, on average, subject to the same attenuation if they travel the same distance from a scattering point to where they are detected.

In use, the re-normalization map N(m), facilitates accounting for the increased probability of detection of an event scattered from breast 12 into detector 16 region outside of breast 12, due to a decrease of path-length through the breast attenuation medium, i.e. the breast tissue.

The re-normalization map is then incorporated in an iterative equation $b^{(n)}$ according to:

$$b^{(n)} = \frac{y}{2^l} + \left(\frac{2^l - 1}{2^l}\right) b^{(n-1)} - \frac{N p * a b_1^{(n-1)}}{2^l} - \frac{p * a b_2^{(n-1)}}{2^l}, \quad \text{Equation 9}$$

where the subscript 1 refers to direct events outside breast 12 boundary, subscript 2 refers to direct events inside breast 12 boundary, and l is an integer that satisfies the condition $\bar{p} < 2^l$. In one embodiment, l is a quantity of sub-iterations.

Figure 4:
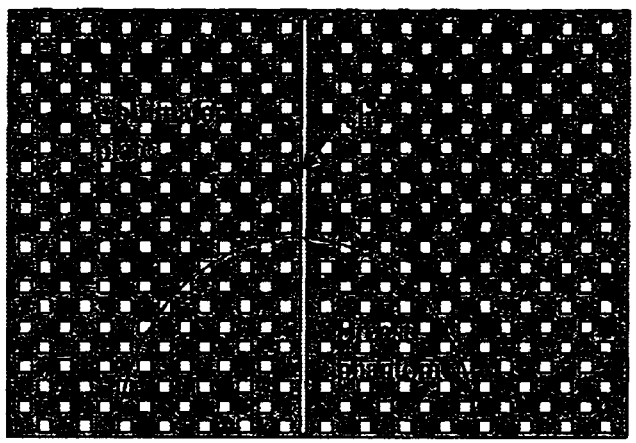
FIG. 4 is an image acquired with a slit collimator using a CIRS breast phantom.
Figure 4:
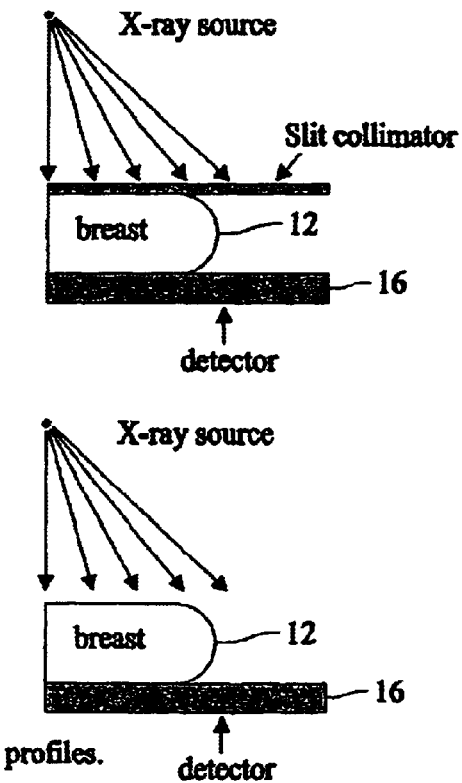

FIG. 4 is an image acquired with a slit collimator using a breast phantom wherein the breast phantom is approximately 5 cm thick and includes approximately 70% glandular 30% fat composition. Data was acquired in open geometry, i.e. without using a slit collimator, and with a slit collimator directly on top of the phantom. The signal directly beneath the slit is almost exclusively due to direct events, i.e., the signal includes no contribution due to scatter. The open-geometry image was processed using the scatter-correction algorithm as described herein, with and without scatter-asymmetry correction.

Figure 5:
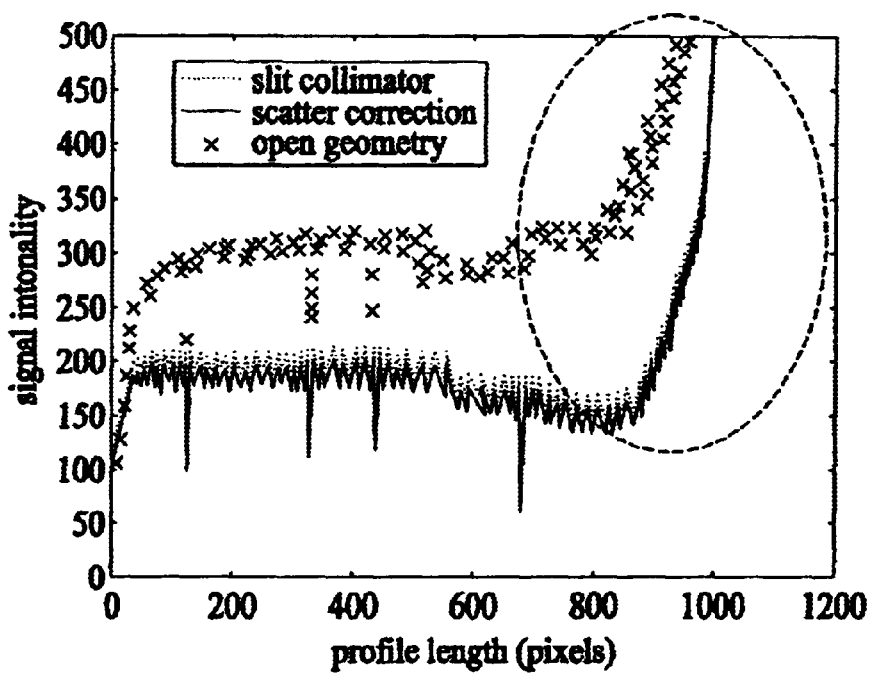
FIG. 5 is a detector profile underneath the slit collimator without correcting for kernel asymmetry.
Figure 6:
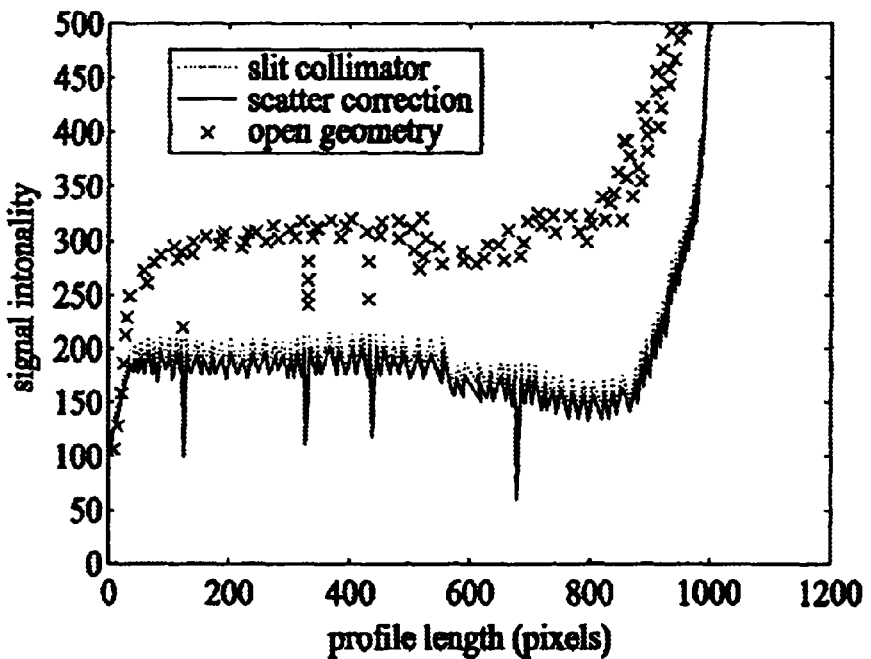
FIG. 6 is a detector profile underneath the slit collimator correcting for kernel asymmetry.

FIG. 5 is a detector profile underneath the slit collimator without correcting for kernel asymmetry. FIG. 6 is a detector profile underneath the slit collimator correcting for kernel asymmetry. FIGS. 5 and 6 show the profiles for pixels underneath the slit collimator for open geometry, scatter-corrected open geometry, and scatter-free images, i.e. slit collimator in use. In use, a mean absolute deviation between scatter-corrected and scatter free images is approximately 3% using the kernel asymmetry correction, and approximately 4% without using the kernel asymmetry correction, for the profile up to breast 12 boundary. In breast 12 boundary region itself, where the intensity varies rapidly between channels, i.e., approximately 800 and approximately 1064 (region demarcated by the ellipse on FIG. 5), the mean absolute deviations were approximately 3% and approximately 5% respectively.

In another exemplary embodiment, a scatter-correction algorithm facilitates removing scatter from an X-ray image, regardless of a relative magnitude of the scatter signal with respect to the direct-events signal. A scatter fraction is defined according to:

$$f_s = \frac{s}{b+s} = \frac{p*b}{b+p*b}, \quad \text{Equation 10}$$

wherein the scatter fraction $f_s$ represents a proportion of scatter events to total events throughout the image. For a given image y, a scatter fraction greater than 0.5 indicates that more scatter events are detected than direct events in a given pixel in the image y, and consequently the norm $\bar{p}$ of the scatter kernel is greater than 1 for that pixel.

Assuming that p is known for a given image acquisition system 10 configuration and object 12 being imaged, and in one embodiment, the scatter kernel p is represented by a sum of Gaussian functions. An initial estimation of the scatter signal can defined as:

$$s^{(0)} = \frac{p*y}{1+\bar{p}} = \frac{p*(b+p*b)}{1+\bar{p}} = \frac{p*b*(\delta+p)}{1+\bar{p}}, \quad \text{Equation 11}$$

where δ denotes the Kronecker delta function.

Equation 12 illustrates redefining a direct image according to:

$$b^{(o)} = y - s^{col} \quad \text{Equation 12}$$

An iterative solution is then defined according to:

$$b^{(n)} = y - p * b^{(n-1)}. \quad \text{Equation 13}$$

Equation 13 reduces to $$b^{(n)} = b - (-1)^n p^{n*}(b^{(0)} - b). \quad \text{Equation 14}$$

For the case of a scatter fraction less than 0.5, i.e. less than 50% of the measured signal is scatter, the norm $\bar{p}$ of the scatter kernel is less than 1.0 and Equation 14 converges toward the direct image b with increasing values of n. However, for $\bar{p} \geq 1$ Equation 14 diverges for increasing values of n and the iterative approach fails to converge toward the direct image b.

In the exemplary embodiment, an initial direct image estimation b is defined as:

$$b^{(0)} = y - s^{(0)} = b + p * b - s^{(0)}. \quad \text{Equation 15}$$

A first interim solution i is calculated according to:

$$i^{(1)(0)} = y - p * b^{(0)}, \quad \text{Equation 16}$$

First interim solution i is averaged with $b^{(0)}$ according to:

$$i^{(1)(1)} = \frac{i^{(1)(0)} + b^{(0)}}{2} \quad \text{Equation 17}$$

Equation 17 is repeated l times to obtain a first iterative solution defined as:

$$b^{(1)} = i^{(1)(l)} = \frac{i^{(1)(l-1)} + b^{(0)}}{2}. \quad \text{Equation 18}$$

A second iteration is performed according to:

$$i^{(2)(0)} = y - p * b^{(1)} = b + p * b - p * b^{(1)}, \quad \text{Equation 19}$$

followed by:

$$i^{(2)(1)} = \frac{i^{(2)(0)} + b^{(1)}}{2}. \quad \text{Equation 20}$$

Averaging l times, a second iterative solution is defined as:

$$b^{(2)} = i^{(2)(l)} = \frac{i^{(2)(l-1)} + b^{(1)}}{2}. \quad \text{Equation 21}$$

Using equations 15 through 21, an initial direct estimation is defined according to:

$$b^{(n)} = \frac{b}{2^l} + \frac{p*b}{2^l} + \left(\frac{2^l-1}{2^l}\delta - \frac{p}{2^l}\right) * b^{(n-1)}, \quad \text{Equation 22}$$

where l is a quantity of averaging operations used in each iteration n, and the first two terms can be expressed as $$\frac{y}{2^l}.$$

Equation 22 is expanded, and the terms collected, according to:

$$b^{(n)} = (\delta + p) * \left(\delta + \sum_{m=1}^{n-1} \alpha^m\right) * \frac{b}{2^l} + \alpha^n * b^{(0)}, \quad \text{Equation 23}$$

where:

$$\alpha = \left(\left(\frac{2^l-1}{2^l}\right)\delta - \frac{p}{2^l}\right). \quad \text{Equation 24}$$

In use, a solution converging toward the direct image b may be acquired by applying Equations 11, 12 and 22, and selecting l such that the scatter kernel norm satisfies $\bar{p}<2^l$.

In one embodiment, the iterative algorithm for scatter correction is of the form $b^{(0)}=y-s^{(0)}$, as initial estimate, with $b^{(n)}=\alpha \cdot b^{(n-1)}+(1-\alpha)\cdot(y-p*b^{(n-1)})$, as iterative update, where α is given by $$\alpha = 1 - \frac{2}{\hat{p}_{min} + \hat{p}_{max} + 2},$$

and $s^{(0)}=p*y$, or some other suitable initial estimate of the scatter contribution in the image. The specific choice of α, where $\hat{p}_{max}=\bar{p}$ and $\hat{p}_{min}$ denote the maximum and minimum values, respectively, of $\hat{p}$, the Fourier transform of p, gives optimal convergence. However, any value of α that satisfies the condition $$\frac{\bar{p}-1}{\bar{p}+1} < \alpha < 1$$

can be used. In use, these equations may be applied to obtain a solution converging toward the direct image. This approach may also be combined with the use of the modulation factor $a_k$, and the use of a re-normalization map as described herein.

In one embodiment, an initial estimate of the direct image, $b^{(0)}=y-s^{(0)}$, is used with an iterative improvement, $b^{(n)}=y-p*b^{(n-1)}$. Combining these equations yields $b^{(n)}=b+(-1)^n p^{n+1}*b+(-1)^{n+1}p^n*s^{(0)}=b+(-1)^n(p^{n+1}*b-p^n*s^{(0)})$. As discussed previously, this approach does not converge if $\bar{p} \geq 1$. However, when adding two intermediate results of this iteration, with suitable weights that add up to one, $\alpha \cdot b^{(n)} + (1-\alpha) \cdot b^{n+1} = b+(-1)^n \cdot (\alpha\delta-(1-\alpha)p)*((p^{n+1}*b-p^n*s^{(0)}))$ can be obtained. Further, by choosing α appropriately, the behavior of the term $(\alpha\delta-(1-\alpha)p)$ one can controlled. In particular its zeros in Fourier space can pre-determined. The undesired term in this last expression is the convolution (or product, in Fourier space) of two terms, the second term being identical to the undesired term in the expression for $b^{(n)}$. Therefore, terms of the form $b^{(n)}$ can be successively combined, as well as suitable linear combinations thereof, to obtain a sequence of images that converges to the direct image. To obtain a sequence of images that converges to the direct image, the weights are chosen such that the zeros in Fourier space are at appropriate locations, and the sum of weights is one.

In one embodiment, a scatter signal $s^{(n)}$ is calculated. The scatter signal estimate $s^{(n)}$ is then used by at least one other scatter-correction algorithm to estimate a direct image $b^{(n)}$.

Figure 7:
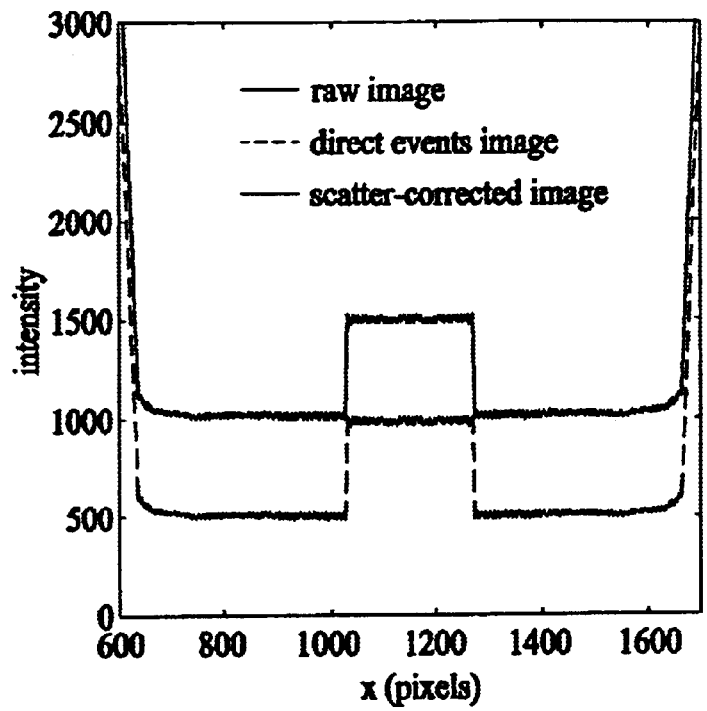
FIG. 7 illustrates the performance of the scatter-correction algorithm described herein.
Figure 8:
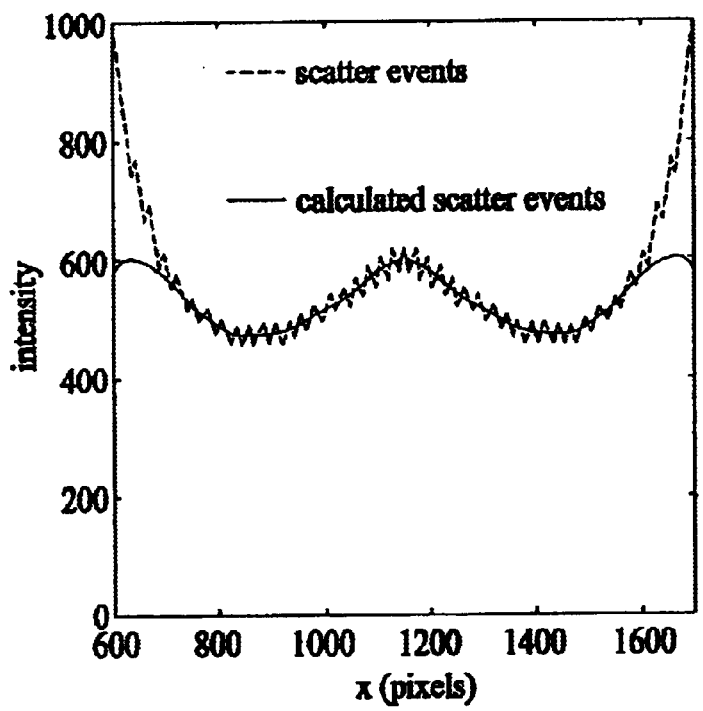
FIG. 8 illustrates the performance of the scatter-correction algorithm described herein.

FIGS. 7 and 8 illustrate the performance of the scatter-correction algorithm described herein on an X-ray phantom image. The phantom includes an acrylic cylinder approximately 5 cm in height with a paraffin core. A discrepancy between the scatter-corrected image and the scatter-free "direct events" data is less than approximately 3% throughout most of the phantom image.

Figure 9:
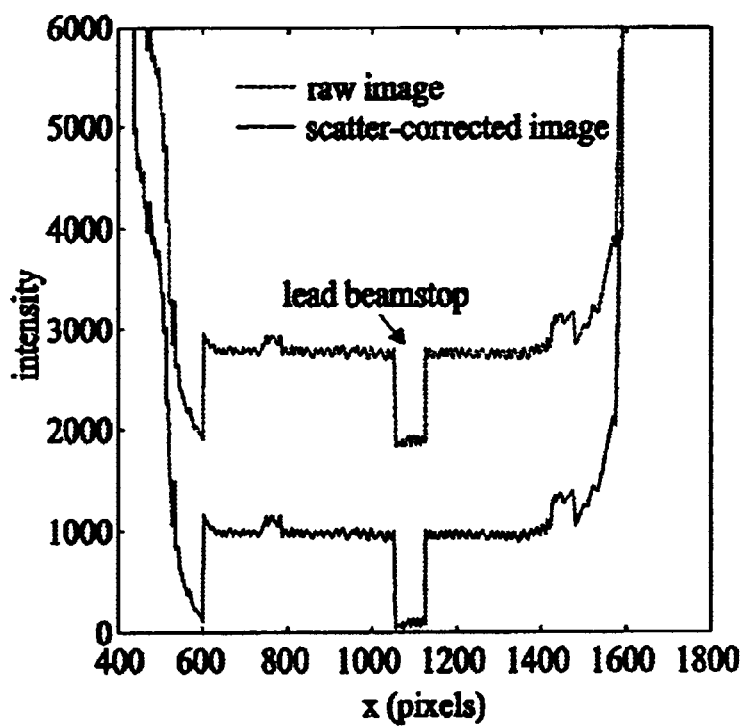
FIG. 9 illustrates the performance of the scatter-correction algorithm described herein.

FIG. 9 illustrates the performance of the scatter-correction algorithm for a breast-tissue equivalent phantom approximately 9 cm thick, wherein the scatter fraction is greater than 0.5, wherein the scatter signal remaining after correction is approximately 5% of the scatter-free images.

While the invention has been described in terms of various specific embodiments, those skilled in the art will recognize that the invention may be practiced with modification within the spirit and scope of the claims.

What is claimed is:

1. A method for removing scatter in an image, said method comprising:

acquiring data of an object of interest; and using an iterative equation including a thickness-dependent kernel modulation factor to reconstruct an image of the object.

2. A method in accordance with claim 1 wherein said using the iterative equation including a thickness-dependent kernel modulation factor comprises using a thickness-dependent modulation factor $a_k$ in accordance with:

$$a_k = \frac{\bar{p}_k}{\bar{p}_{k_0}},$$

where:

$\bar{p}_k$ is a norm of a scatter kernel p; and $\bar{p}_{k_0}$ is a norm of a scatter kernel for a compression thickness of the object.

3. A method in accordance with claim 1 further comprising estimating a kernel re-normalization map for use in the iterative equation.

4. A method in accordance with claim 3 wherein estimating the kernel re-normalization map comprises estimating the re-normalization map according to $N(m) \sim e^{\mu d_b(m)}$:

where:

N(m) is the re-normalization map of a pixel m;

μ is a mean attenuation coefficient for an X-ray photon spectrum in breast equivalent material; and $d_b(m)$ is a distance between pixel m and a closest pixel belonging to an object boundary.

5. A method in accordance with claim 3 wherein estimating the kernel re-normalization map for use in the iterative equation comprises incorporating the kernel re-normalization map into the iterative equation $b^{(n)}$ according to:

$$b^{(n)} = \frac{y}{2^l} + \left(\frac{2^l-1}{2^l}\right)b^{(n-1)} - \frac{Np*ab_1^{(n-1)}}{2^l} - \frac{p*ab_2^{(n-1)}}{2^l}.$$

where:
y is a measured image;
p is a scatter kernel;
$\overline{P}_k$ is a norm of a scatter kernel p;
l is an integer that satisfies the condition $\overline{p}<2^l$;
subscript 1 is the direct events outside of the object boundary;
subscript 2 is the direct events inside the object boundary;
α is the kernel modulation factor;
N is the kernel re-normalization map;
$b^n$ is an estimate of the image formed by directly transmitted photons; and
n is a quantity of iterations.

6. A method in accordance with claim 3 wherein estimating a re-normalization map for use in the iterative equation comprises estimating a re-normalization map for each pixel outside of the breast boundary by calculating a distance between the pixel and a closest pixel belonging to the breast boundary.

7. A method in accordance with claim 1 wherein using an iterative equation including a thickness-dependent kernel modulation comprises using an iterative equation including a compressed breast thickness-dependent kernel modulation factor to reconstruct an image of the object.

8. A method in accordance with claim 1 further comprising subtracting a scatter signal estimate from a measured image during each iteration.

9. A method in accordance with claim 8 wherein subtracting a scatter signal estimate comprises subtracting a scatter signal estimate generated using at least one convolution.

10. A method in accordance with claim 9 wherein using at least one convolution comprises using at least one convolution computed in Fourier space.

11. A method in accordance with claim 9 wherein using at least one convolution comprises using two one-dimensional convolutions.

12. A method in accordance with claim 1 further comprising estimating a scatter signal and using the scatter signal estimate in a scatter correction algorithm to estimate a direct image.

13. A medical imaging system for removing scatter in an image, said medical imaging system comprising:
a detector array;
at least one radiation source; and
a computer coupled to said detector array and radiation source and configured to:
acquire data of an object of interest;
estimate a re-normalization map according to N(m) $\sim e^{\mu d_b(m)}$:
where:
N(m) is the re-normalization map of a pixel m;
μ is a mean attenuation coefficient for an X-ray photon spectrum in breast equivalent material; and
$d_b(m)$ is a distance between pixel m and a closest pixel belonging to an object boundary;
use an iterative equation including a thickness-dependent kernel modulation factor in accordance with $$a_k = \frac{\overline{p}_k}{\overline{p}_{k_0}},$$

where:
$\overline{p}_k$ is a norm of a scatter kernel p; and
$\overline{p}_{k_0}$ is a norm of a scatter kernel for a compression thickness of the object; and
incorporate the re-normalization map into the iterative equation $b^{(n)}$ according to:

$$b^{(n)} = \frac{y}{2^l} + \left(\frac{2^l-1}{2^l}\right)b^{(n-1)} - \frac{Np*ab_1^{(n-1)}}{2^l} - \frac{p*ab_2^{(n-1)}}{2^l}.$$

where:
y is a measured image;
p is a scatter kernel;
$\overline{p}_k$ is a norm of a scatter kernel p;
l is an integer that satisfies the condition $\overline{p}<2^l$;
subscript 1 is the direct events outside of the object boundary;
subscript 2 is the direct events inside the object boundary;
α is the kernel modulation factor;
N is the kernel re-normalization map;
$b^n$ is an estimate of the image formed by directly transmitted photons; and
n is a quantity of iterations.

14. A method for removing scatter in an image, said method comprising:
acquiring data of an object of interest; and
using an iterative equation to reconstruct an image of the object when a scatter fraction is greater than approximately 0.5.

15. A method in accordance with claim 14 further comprising:
defining an initial scatter kernel estimation;
re-defining an initial (zeroth estimate) of a direct image
re-defining the direct image; and
defining an initial direct estimation using the initial scatter kernel estimation and the re-defined direct image.

16. A method in accordance with claim 14 further comprising selecting a quantity l such that $\overline{p}<2^l$:
where:
$\overline{p}$ is the scatter kernel norm; and
l is an integer that satisfies the condition $\overline{p}<2^l$.

17. A method in accordance with claim 14 further comprising selecting an iterative equation such that:
$b^{(0)}=y-S^{(0)}$, is an initial estimate, with
$b^{(n)}=\alpha \cdot b^{(n-1)}+(1-\alpha)\cdot(y-p*b^{(n-1)})$, is an iterative update, where
$s^{(0)}=p*y$.
wherein:
y is a measured image;
p is a scatter kernel;
α is the kernel modulation factor;
N is the kernel re-normalization map;
$b^n$ is an estimate of the image formed by directly transmitted photons; and
n is a quantity of iterations.

18. A method in accordance with claim 17 further comprising selecting α such that $$\frac{\bar{p}-1}{\bar{p}+1} < \alpha < 1.$$

19. A method in accordance with claim 17 further comprising selecting α such that $$\alpha = 1 - \frac{2}{\hat{p}_{min} + \hat{p}_{max} + 2},$$

where $\hat{p}_{max}=\bar{p}$ and $\hat{p}_{min}$ are the maximum and minimum values, respectively, of $\hat{p}$, the Fourier transform of p.

20. A method in accordance with claim 15 wherein defining an initial scatter estimation comprises defining an initial scatter estimation $s_{(0)}$ in accordance with $$s^{(0)} = \frac{p*y}{1+\bar{p}} = \frac{p*(b+p*b)}{1+\bar{p}} = \frac{p*b*(\delta+p)}{1+\bar{p}},$$

where:
y is a measured image;
δ is the Kronecker delta function;
p is a scatter kernel;
$\bar{p}$ is a scatter kernel norm;
l is an integer that satisfies the condition $\bar{p}<2^l$; and
b is a direct image.

21. A method in accordance with claim 15 wherein defining an initial direct estimation comprises defining an initial direct estimation in accordance with $$b^{(n)} = \frac{b}{2^l} + \frac{p*b}{2^l} + \left(\frac{2^l-1}{2^l}\delta - \frac{p}{2^l}\right)*b^{(n-1)},$$

where:
δ is the Kronecker delta function;
p is a scatter kernel;
n is a quantity of iterations;
l is an integer that satisfies the condition $\bar{p}<2^l$; and
$b^n$ is an estimate of the image formed by directly transmitted photons.

22. A method in accordance with claim 15 wherein re-defining a direct image comprises re-defining a direct image in accordance with $b^{(0)}=y-s^{(0)}$,
where:
b is a direct image;
S is a scatter image; and
y is an image including the direct image and the scatter image.

23. A computer readable medium encoded with a program executable by a computer for removing scatter from an image, said program configured to instruct the computer to:
acquire data of an object of interest; and
define an initial scatter signal estimation in accordance with $$s^{(0)} = \frac{p*y}{1+\bar{p}} = \frac{p*(b+p*b)}{1+\bar{p}} = \frac{p*b*(\delta+p)}{1+\bar{p}},$$

where:
y is a measured image;
δ is the Kronecker delta function;
p is a scatter kernel;
$\bar{p}$ is a scatter kernel norm;
l is an integer that satisfies the condition $\bar{p}<2^l$;
b is a direct image;
re-define a direct image;
define an initial direct estimation in accordance with $$b^{(n)} = \frac{b}{2^l} + \frac{p*b}{2^l} + \left(\frac{2^l-1}{2^l}\delta - \frac{p}{2^l}\right)*b^{(n-1)};$$

where:
n is a quantity of iterations;
use an iterative equation to reconstruct an image of the object when a scatter fraction is greater than approximately 0.5; and
select a sub-iteration quantity l such that $\bar{p}<2^l$.

24. A computer readable medium encoded with a program executable by a computer for removing scatter from an image, said program configured to instruct the computer to:
acquire data of an object of interest; and
use an iterative equation including a thickness-dependent kernel modulation factor to reconstruct an image of the object.

25. A computer readable medium in accordance with claim 23 wherein to use the iterative equation including a thickness-dependent kernel modulation factor, said program configured to use a thickness-dependent modulation factor $\alpha_k$ in accordance with:

$$a_k = \frac{\bar{p}_k}{\bar{p}_{k_0}},$$

where:
$\bar{p}_k$ is a norm of a scatter kernel p; and
$\bar{p}_{k_0}$ is a norm of a scatter kernel for a compression thickness of the object.

26. A computer readable medium in accordance with claim 23 wherein said program further configured to estimate a re-normalization map for use in the iterative equation.

27. A computer readable medium in accordance with claim 25 wherein to estimate the re-normalization map, said computer further configured to estimate the re-normalization map according to $N(m) \sim e^{\mu d_b(m)}$:
where:
N(m) is the re-normalization map of a pixel m;
μ is a mean attenuation coefficient for an X-ray photon spectrum in breast equivalent material; and
$d_b(m)$ is a distance between pixel m and a closest pixel belong to an object boundary.

28. A computer readable medium in accordance with claim 25 wherein to estimate the re-normalization map for use in the iterative equation, said program further configured to incorporate the re-normalization map into the iterative equation $b^{(n)}$ according to:

$$b^{(n)} = \frac{y}{2^l} + \left(\frac{2^l-1}{2^l}\right)b^{(n-1)} - \frac{Np*ab_1^{(n-1)}}{2^l} - \frac{p*ab_2^{(n-1)}}{2^l}.$$

where:
p is a scatter kernel;
l is an integer that satisfies the condition $\bar{p}<2^l$;
subscript 1 is the direct events outside of the object boundary;

subscript 2 is the direct events inside the object boundary;

α is the kernel modulation factor;

N is the kernel re-normalization map;

$b^n$ is an estimate of the image formed by directly transmitted photons; and n is a quantity of iterations.

29. A computer readable medium in accordance with claim 25 wherein to estimate a re-normalization map for use in the iterative equation, said program further configured to estimate a re-normalization map for each pixel outside of the breast boundary by calculating a distance between the pixel and a closest pixel belonging to the breast boundary.

30. A medical imaging system for removing scatter in an image, said medical imaging system comprising:

a detector array;

at least one radiation source; and a computer coupled to said detector array and radiation source and configured to:

acquire data of an object of interest; and use an iterative equation to reconstruct an image of the object when a scatter fraction is greater than approximately 0.5.

31. A medical imaging system in accordance with claim 30 wherein said computer further configured to:

define an initial scatter kernel estimation;

re-define a direct image; and define an initial direct estimation using the initial scatter kernel estimation and the re-defined direct image.

32. A medical imaging system in accordance with claim 30 wherein said computer further configured to select a quantity l such that $\bar{p} < 2^l$:

where:

$\bar{p}$ is the scatter kernel norm; and l is an integer that satisfies the condition $\bar{p} < 2^l$.

33. A medical imaging system in accordance with claim 31 wherein to define an initial scatter estimation, said computer further configured to define an initial scatter estimation $s^{(0)}$ in accordance with $$s^{(0)} = \frac{p*y}{1+\bar{p}} = \frac{p*(b+p*b)}{1+\bar{p}} = \frac{p*b*(\delta+p)}{1+\bar{p}},$$

where:

δ is the Kronecker delta function;

p is a scatter kernel;

$\bar{p}$ is a scatter kernel norm; and b is a direct image.

34. A medical imaging system in accordance with claim 31 wherein to define an initial direct estimation, said computer further configured to define an initial direct estimation in accordance with $$b^{(n)} = \frac{b}{2^l} + \frac{p*b}{2^l} + \left(\frac{2^l-1}{2^l}\delta - \frac{p}{2^l}\right)*b^{(n-1)},$$

where:

δ is the Kronecker delta function;

p is a scatter kernel;

l is an integer that satisfies the condition $\bar{p} < 2^l$;

$b^n$ is an estimate of the image formed by directly transmitted photons; and n is a quantity of iterations.

35. A medical imaging system in accordance with claim 31 wherein to re-define a direct image, said computer further configured to re-define a direct image in accordance with $b^{(0)} = y - s^{(0)}$, where:

b is a direct image;

s is a scatter image; and y is an image including the direct image and the scatter image.

* * * * *

UNITED STATES PATENT AND TRADEMARK OFFICE
CERTIFICATE OF CORRECTION

PATENT NO.    : 6,633,626 B2
DATED         : October 14, 2003
INVENTOR(S)   : Trotter et al.

It is certified that error appears in the above-identified patent and that said Letters Patent is hereby corrected as shown below:

Column 11,
Line 11, delete "$\overline{P}_k$" and insert therefor -- $\overline{p}_k$ --.

Line 13, remove bold font on "1".
Line 15, remove bold font on "2".

Column 12,
Line 8, delete "$\overline{p}_{k_00}$" and insert therefor -- $\overline{p}_{k_0}$ --.

Line 55, delete "S" and insert therefor -- s --.

Column 13,
Line 18, delete "$s_{(0)}$" and insert therefor -- $s^{(0)}$ --.
Line 51, delete "S is a scatter" and insert therefor -- s is a scatter --.

Column 14,
Line 66, remove bold font on "1".

Column 15,
Line 1, remove bold font on "2".

Signed and Sealed this

Twenty-fourth Day of February, 2004

JON W. DUDAS
*Acting Director of the United States Patent and Trademark Office*